(12) United States Patent
Haas et al.

(10) Patent No.: US 6,441,255 B1
(45) Date of Patent: Aug. 27, 2002

(54) METHOD OF PRODUCING ALCOHOLS BY CATALYTIC HYDROGENATION OF ALDEHYDES OR KETONES

(75) Inventors: Thomas Haas, Frankfurt; Bernd Jaeger, Darmstadt; Jörg Sauer, Rodenbach; Rudolf Vanheertum, Kahl, all of (DE)

(73) Assignee: Degussa -Huls AG, Frankfurt am Main (DE)

( * ) Notice: Subject to any disclaimer, the term of this patent is extended or adjusted under 35 U.S.C. 154(b) by 0 days.

(21) Appl. No.: 09/406,137

(22) Filed: Sep. 27, 1999

(30) Foreign Application Priority Data

Sep. 28, 1998 (DE) .......................................... 198 44 325

(51) Int. Cl.⁷ .......................................... C07C 29/141
(52) U.S. Cl. ...................................... 568/881; 568/914
(58) Field of Search ................................ 568/863, 881, 568/914; 502/325, 332; 549/430

(56) References Cited

U.S. PATENT DOCUMENTS

| | | | |
|---|---|---|---|
| 3,144,490 A | 8/1964 | Rylander | 260/618 |
| 4,413,152 A | 11/1983 | Arena | 568/863 |
| 4,487,980 A | 12/1984 | Arena | 568/863 |
| 4,520,211 A | 5/1985 | Lepper | 568/863 |
| 4,777,302 A | 10/1988 | Haji | 568/862 |
| 4,933,473 A | 6/1990 | Ninomiya | 568/862 |
| 5,451,390 A | 9/1995 | Hartmann | 423/610 |
| 5,495,055 A | 2/1996 | Rueter | 568/876 |
| 5,902,916 A | 5/1999 | Ruhl | 585/266 |

FOREIGN PATENT DOCUMENTS

| | | |
|---|---|---|
| DE | 37 26 195 A1 | 2/1988 |
| DE | 19 37 190 | 8/1997 |
| EP | 0 319 208 A1 | 6/1989 |
| EP | 0 803 488 A2 | 10/1997 |
| FR | 2 526 782 | 11/1983 |
| JP | 2573687 | 1/1997 |
| WO | WO 98/57913 | 12/1998 |

OTHER PUBLICATIONS van Bekkum et al., "Carbohydrates as Organic Raw Materials III" (1996), pp. 52–54.
Arena, Blaise J., "Deactivation of Ruthenium Catalysts in Continuous Glucose Hydrogenation", Applied Catalysis A: Mineral 87 (1992), pp. 219–229.
Database WPI, Sec. Ch, Week 199101, Derwent Publications Ltd., London, GB; Class E17 AN 1991–003139 XP002133816 & JP 02 279643 A (Mitsubishi Petrochemical Co. Ltd.), Nov. 15, 1990.
English language abstract of OR above Jan. 22, 1997.

*Primary Examiner*—Sreeni Padmanabhan
(74) *Attorney, Agent, or Firm*—Pillsbury Winthrop LLP

(57) ABSTRACT

Carrier-bound ruthenium catalysts are used to produce alcohols by the catalytic hydrogenation of aldehydes and ketones. The problem of deactivation of the catalyst is solved by the use of a ruthenium catalyst on an oxide carrier of the series $TiO_2$, $SiO_2$, $ZrO_2$, MgO, mixed oxides thereof and silicates thereof. In particular, Ru on $TiO_2$ or $SiO_2$ results in a long service life of the catalyst.

7 Claims, No Drawings

METHOD OF PRODUCING ALCOHOLS BY CATALYTIC HYDROGENATION OF ALDEHYDES OR KETONES

CROSS-REFERENCE TO RELATED APPLICATION

This application relates to German Application DE 109 44 325.0, filed Sep. 28, 1998, which disclosure is incorporated herein by reference.

FIELD OF THE INVENTION

The invention relates to a method of producing alcohols by catalytic hydrogenation of aldehydes or ketones using an Ru carrier catalyst. The catalyst to be used in accordance with the invention is deactivated to a rather slight extent and therefore has a higher service life than Ru carrier catalysts previously used for this purpose.

BACKGROUND OF THE INVENTION

The conversion of aldehydes and ketones into the corresponding alcohols by catalytic hydrogenation is known. Nickel carrier catalysts or Raney nickel are frequently used as catalysts for the hydrogenation of aldehydes and ketones. A disadvantage of such catalysts is the Ni leaching, during which Ni passes in dissolved form into the liquid reaction medium. This renders the workup of the reaction mixture difficult and the leached-out Ni must be removed, e.g., burned, with other byproducts, leaving carcinogenic NiO.

In order to avoid the problems cited, carrier-bound noble-metal catalysts, especially Ru catalysts, have been used. B. J. Arena (Applied Catalysis A 87 (1992) 219–229) teaches the use of Ru catalysts on aluminum oxide for the hydrogenation of glucose to sorbitol. A disadvantage of this catalyst is the short effective service life caused by deactivation. During the deactivation of Ru—$Al_2O_3$ not only deactivating components such as iron, sulfur and gluconic acid are deposited on the catalyst but at the same time the properties of the Ru carrier and of the $Al_2O_3$ carrier change, which manifest themselves in, among other things, an agglomeration of the Ru and a reduction of the BET surface of the $Al_2O_3$. In order to reduce the deactivation, additional purification measures of the feed materials and/or frequent regeneration of the catalyst are necessary, which renders the method more complicated and/or less economical.

According to "Carbohydrates as Organic Raw Materials III", ed. by H. van Bekkum et al. (1996) 52–54 sorbitol can be obtained from polysaccharides such as starch, during which the hydrolysis of the polysaccharide and the hydrogenation of the released glucose take place at the same time by hydrogenation in the presence of an Ru carrier catalyst with H-USY zeolite as carrier. The carrier acts as acid catalyst. According to this document similar results are achieved if a combination of 5% Ru on activated carbon as hydrogenation catalyst and zeolite-ZSM 5 as acid catalyst is used. No indications about the effective service life of the catalyst can be gathered from this document.

According to U.S. Pat. No. 4,933,473 hydroxypivalaldehyde or its dimer can be converted by catalytic hydrogenation into neopentylglycol. A combination of platinum, ruthenium and tungsten in a certain amount ratio serves as catalyst. This catalytically active metal combination can also be used on a carrier from the series of $SiO_2$, $Al_2O_3$, MgO, $TiO_2$, $ZrO_2$, zeolites, carbon, silicon carbide and diatomaceous earth. The selectivity is the highest when Pt/Ru/W-activated carbon is used and drops off sharply in the series $Al_2O_3$, $SiO_2$, $TiO_2$ as carrier. Neither the examples nor reference examples concern the use of a catalyst on the basis of Ru as the sole noble metal on an oxide carrier.

As was determined by the inventors of this application, the conversion and selectivity and especially the catalytic service life are insufficient in many instances when using Ru activated carbon in the generic hydrogenation. Reference has already been made to the problems which result when Ru—$Al_2O_3$ is used.

SUMMARY OF THE INVENTION

Accordingly, the present invention solves the problem by making available an improved method for the catalytic hydrogenation of aldehydes and ketones to the corresponding alcohols. The improvement is directed to the raising of the service life of the carrier-bound Ru catalyst to be used.

A method of producing an alcohol by the catalytic hydrogenation of the corresponding aldehyde, except 3-hydroxypropionaldehyde, or ketone in aqueous or organic solution at a temperature of 20° to 200° C. and an $H_2$ pressure of 0.5 to 30 MPa using a carrier-bound ruthenium catalyst was found which is characterized in that ruthenium on an oxide carrier selected from the group $TiO_2$, $SiO_2$, $ZrO_2$, MgO, mixed oxides thereof and silicates thereof, except zeolites, with a ruthenium content of 0.1 to 20% by weight is used as catalyst.

The advantageous use of a ruthenium catalyst with the oxide carrier materials has already been recognized in the method of producing 1,3-propane diol from 3-hydroxypropionaldehyde according to the not yet published DE patent application 197 37 190.6. However, the use of these catalysts is not limited, as has now been found, to the hydrogenation of 3-hydroxypropionaldehyde. The disclosure of DE patent application 197 37 190.6 is therefore incorporated by reference to its full extent in the disclosure of the present application.

Ruthenium catalysts on oxide carriers to be used in accordance with the invention are described, e.g., in "Catalyst Supports and Supported Catalysts" by Alvin B. Stiles, Butterworth 1987, chapters 2 and 3. The coating of the oxide carrier can take place especially advantageously by means of the "incipient wetness method"—see "Preparation of Catalyst" ed. By B. Delmon, P. A. Jacobs, G. Poncald, Amsterdam Elsevier 1976, page 13.

The water absorption capacity of the carrier is determined for this. Thereafter, an aqueous ruthenium chloride solution with a concentration corresponding to the ruthenium coating to be formed is produced. The carrier is charged with aqueous ruthenium chloride in accordance with the water absorption capacity. The charged carrier is subsequently dried, preferably at 20° to 100° C., at normal pressure in an atmosphere of inert gas such as neon, helium, argon or air, reduced with hydrogen at a temperature of preferably 100° to 500° C. for 20 min to 24 hrs using a gaseous mixture of $H_2/N_2$ containing 1 to 100% by volume hydrogen, and washed free of chlorine, if necessary, preferably to a chlorine content of <100 ppm $Cl^-$.

According to a preferred embodiment the carrier is based on titanium dioxide or silicon dioxide. A pyrogenically produced $TiO_2$, especially a $TiO_2$ produced by flame hydrolysis, is preferably used as the carrier.

For example, a pyrogenic titanium dioxide obtained by flame hydrolysis from titanium tetrachloride with a BET surface of 40 to 60 $m^2/g$ and a total pore volume of 0.25 to 0.75 ml/g can be used as the carrier. This carrier may have an average size of the primary particles of 20 nm, a density of 3.7 g/cm$^3$ and an X-ray structure of 20 to 40% rutile and 80 to 60% anatase and with impurities of silicon dioxide, aluminum oxide and iron oxide that are below 0.5% by weight. Pyrogenic titanium oxide-like material, for example, P25 produced by Degussa-Hüls AG, is especially suitable as a carrier for the catalytically active component. This carrier has a high specific surface with a BET of on the average 50 m$^2$/g (measured according to DIN 66131).

The Ru coating of the carrier is in a range of 0.1 to 20% by weight, preferably 0.5 to 10% by weight and especially preferably 1 to 5% by weight.

The hydrogenation can be carried out in a customary manner, either discontinuously or continuously. The catalyst can be suspended thereby in the liquid reaction medium. Alternatively, the catalyst is used in the form of molded bodies such as pellets, granulates, spheres, extruded blanks and arranged in a reactor as a fixed bed. This fixed-bed reactor can be operated in a flooded state as a bubble reactor but is preferably operated as a trickle-bed reactor.

One skilled in the art will adapt the conditions of pressure and temperature to the substrate to be hydrogenated. It is an advantage of the catalysts to be used in accordance with the invention that their high activity makes mild reaction conditions possible in general, such as 20° to 100° C. and 1 to 10 MPa, especially 2 to 5 MPa H$_2$ pressure.

The aldehydes and ketones to be hydrogenated can have any structure, such as, aliphatic, aromatic, heteroaromatic, aliphatic-aromatic or aliphatic-heteroaromatic. They can also contain other functional groups, and it should be determined beforehand whether these functional groups should remain unchanged or should be hydrogenated themselves. According to a preferred embodiment, carbohydrates and other carbonyl compounds containing one or more hydroxyl groups are converted into polyols.

The aldehyde or ketone substrate can be hydrogenated per se, if it is liquid, or can be hydrogenated dissolved in a solvent. Solvents can be organic or aqueous or represent mixtures. Water is especially preferred as a solvent, to which organic solutizers can be added as needed.

It is known that acetals and ketals can be produced in the reduction of aldehydes and ketones. In order to split these byproducts in situ and convert them completely into the desired alcohol it is purposeful to carry out the hydrogenation in the presence of an acidic catalyst. This acidic catalyst can be dissolved—e.g., in the case of a mineral acid—or be present undissolved as solid acid. At an elevated reaction temperature the preferred carriers, SiO$_2$ and TiO$_2$, act themselves as acids.

The ruthenium catalysts bound to oxide carriers in accordance with the invention have a surprisingly long service life since they deactivate much more slowly than previously used, carrier-bound Ru catalysts. This improves the economy of the method since the activity remains preserved for a long time and non-productivity time periods for catalytic regeneration are minimized. The space-time yield is thus increased.

DETAILED DESCRIPTION OF THE INVENTION

The following examples and reference examples illustrate the invention.

The catalysts were tested under stationary conditions in order to also be able to determine the long-term behavior. The hydrogenation was carried out continuously in a trickle-bed system with 140 ml reactor volume. The system comprised a liquid receiver, the reactor and a liquid separator. The reaction temperature was adjusted via a heat-carrier circuit. Pressure and hydrogen current were regulated electronically. The aqueous solution of the substrate (aldehyde or ketone) was charged to the hydrogen current with a pump and the mixture put onto the head of the reactor (trickle-bed method of operation). After having passed through the reactor the product formed was removed at regular intervals from the separator. The concentration of the aldehyde or ketone in the educt solution, the temperature, H$_2$ pressure and the liquid charging LHSV 1 h$^{-1}$ can be gathered from the following examples. The results of the tests are collated in tables 1 and 2.

EXAMPLES (B) 1 to 2 AND COMPARATIVE EXAMPLES (VB) 1 to 3

Examples 1 and 2 use the Ru carrier catalysts to be employed in accordance with the invention. These Examples concern, as do Comparative Examples 1 to 3, the hydrogenation of 3-hydroxypropionaldehyde to 1,3-propane diol, which, considering the still not published DE 197 37 190.6, is not claimed. The reaction temperature was 40° C., the H$_2$ pressure 4 MPa, the aldehyde concentration of the aqueous solution 10% by weight and the LHSV value 1 h$^{-1}$. The surprising activity of the catalysts used in accordance with the invention is clear from Table 1 and results in generally greater conversion, but especially results in better long-term stability, in comparison to the non-inventive catalysts as used in the Comparative Examples.

TABLE 1

| Example No. | Catalyst | Operating time (h) | Conversion (%) | Conversion decrease (%/h) |
| --- | --- | --- | --- | --- |
| B 1.1 | 5% Ru on TiO$_2$ (P 25 of Degussa-Hüls AG; extruded blanks d = 1 mm) | 19 | 84 | |
| B 1.2 | 5% Ru on TiO$_2$ (P 25 of Degussa-Hüls AG; extruded blanks d = 1 mm) | 233 | 84 | 0 |
| B 2.1 | 5% Ru on SiO$_2$ (silica gel V 432 of the Grace Co.: d = 0.8–1.2 mm) | 48 | 90 | |
| B 2.2 | 5% Ru on SiO$_2$ (silica gel V 432 of the Grace Co.: d = 0.8–1.2 mm) | 434 | 89 | 0.26 |
| VB 1.1 | 10% Ru on Al$_2$O$_3$ (Speralite 521 of the Rhone-Poulenc Co.); d = 1.1–1.3 mm | 72 | 79 | |
| VB 1.2 | 10% Ru on Al$_2$O$_3$ (Speralite 521 of the Rhone-Poulenc Co.); d = 1.1–1.3 mm | 240 | 77 | 1.19 |
| VB 2.1 | 5% Ru on activated carbon (Norite ROX; d = 0.8 mm) | 24 | 99.7 | |
| VB 2.2 | 5% Ru on activated carbon (Norite ROX; d = 0.8 mm) | 96 | 60 | 55.13 |
| VB 3.1 | 2% Pt on TiO$_2$ (P 25 of Degussa-Hüls AG; d = 1 mm) | 20 | 60 | |
| VB 3.2 | 2% Pt on TiO$_2$ (P 25 of Degussa-Hüls AG; d = 1 mm) | 300 | 45 | 5.36 |

Examples (B) 3 to 6 and Comparative Examples (VB) 4 to 7

Table 2 shows the results—conversion and selectivity—of the hydrogenation of different educts as a function of the operating time and catalyst; the reaction temperature (T) and the LHSV value are also shown. The concentration of the educt in water was 10% by weight, the H$_2$ pressure 4 MPa.

TABLE 2

| No. | Educt | Product | Catalyst | Operating time (h) | Temperature (° C.) | LHSV (h$^{-1}$) | Conversion (%) | Selectivity (%) |
|---|---|---|---|---|---|---|---|---|
| B 3.1 | Hydroxy acetone | 1,2-propane diol | 2% Ru on TiO$_2$*) | 84 | 51 | 3.0 | 51 | 94 |
| B 3.2 | " | " | " | 251 | 50 | 3.1 | 56.2 | 96 |
| VB 4 | " | " | 2% Ru on AK**) | 24 | 48 | 3.1 | 7.3 | |
| B 4.1 | propanal | 1-propanol | 2% Ru on TiO$_2$*) | 17 | 50 | 3.5 | 75.9 | 94 |
| B 4.2 | " | " | " | 348 | 50 | 3.1 | 75.1 | 94 |
| VB 5.1 | " | " | 5% Ru on AK**) | 48 | 53 | 2.8 | 94.1 | 94 |
| VB 5.2 | " | " | " | 88 | 51 | 2.9 | 68.8 | 93 |
| B 5 | glucose | sorbitol | 2% Ru on TiO$_2$*) | 118 | 40 | 3.3 | 94.8 | 69.4 |
| VB 6 | " | " | 2% Ru on AK**) | 160 | 40 | 2 | 76.4 | 11.6 |
| B 6 | acetone | 2-propanol | 2% Ru on TiO$_2$*) | 63 | 50 | 3.2 | 99.4 | 99.7 |
| VB 7 | " | " | 5% Ru on AK**) | 43 | 51 | 3.2 | 96.6 | 98.0 |

*)TiO$_2$ (P 25 of Degussa-Hüls AG), extruded blanks, diameter d = 1 mm
**)AK = activated carbon (Norite ROX), d = 0.8 mm Usually, higher conversions are achieved after a few hours operating time using the Ru catalysts on TiO$_2$ in comparison to Ru on activated carbon. It is remarkable that these high conversions and selectivities are essentially maintained even after a long operating time.

What is claimed is:

1. A method for producing an alcohol, comprising:
   catalytic hydrogenation of the appropriate aldehyde, except 3-hydroxypropion aldehyde, or ketone in aqueous or organic solution at a temperature of 20 to 53° C. and an H$_2$ pressure of 0.5 to 30 MPa using a carrier-bound ruthenium catalyst,
   wherein the catalyst comprises ruthenium on an oxide carrier selected from the group consisting of TiO$_2$, SiO$_2$, ZrO$_2$, MgO, mixed oxides thereof and silicates thereof, except zeolites, wherein the catalyst has a ruthenium content of 0.1 to 20% by weight.

2. The method according to claim 1, wherein the catalyst comprises Ru on a TiO$_2$ or SiO$_2$ carrier.

3. The method according to claim 1 or 2, wherein the catalyst comprises Ru on a pyrogenic TiO$_2$ carrier.

4. The method according to claim 3, wherein the pyrogenic TiO$_2$ carrier is produced by flame hydrolysis.

5. The method according to claim 1, comprising:
   producing polyols by hydrogenation of carbonyl group of carbohydrates.

6. The method according to claim 1, wherein the hydrogenation is carried out in the presence of a homogeneous or heterogeneous acidic catalyst.

7. The method according to claim 1, wherein the hydrogenation is carried out in a trickle-bed reactor.

* * * * *